United States Patent [19]
Lewis et al.

[11] Patent Number: 6,005,130
[45] Date of Patent: Dec. 21, 1999

[54] METHOD FOR MAKING ALKYLHALOSILANES

[75] Inventors: Larry Neil Lewis, Scotia; John Matthew Bablin, Amsterdam, both of N.Y.

[73] Assignee: General Electric Company, Schenectady, N.Y.

[21] Appl. No.: 09/161,637

[22] Filed: Sep. 28, 1998

[51] Int. Cl.$^6$ ...................................................... C07F 7/16
[52] U.S. Cl. ............................................................ 556/422
[58] Field of Search ............................................. 556/472

[56] References Cited

U.S. PATENT DOCUMENTS

| | | |
|---|---|---|
| 2,380,995 | 7/1945 | Rochow . |
| 4,500,724 | 2/1985 | Ward . |
| 4,602,101 | 7/1986 | Halm et al. . |
| 4,762,940 | 8/1988 | Halm et al. . |
| 4,898,960 | 2/1990 | Dossaj et al. . |
| 4,946,978 | 8/1990 | Halm et al. . |
| 5,059,343 | 10/1991 | Halm et al. . |
| 5,059,706 | 10/1991 | Degen et al. . |
| 5,068,385 | 11/1991 | Degen et al. . |
| 5,223,586 | 6/1993 | Mautner et al. . |
| 5,596,119 | 1/1997 | Halm et al. . |
| 5,714,131 | 2/1998 | Margaria et al. . |
| 5,874,604 | 2/1999 | Steiner et al. ...................... 556/472 |

FOREIGN PATENT DOCUMENTS 3523541  1/1987  Germany .

OTHER PUBLICATIONS

"Commercial Production of Silanes by the Direct Synthesis", B. Kanner and K. M. Lewis, K.M. Lewis and D.G. Rethwisch (Eds.), Catalyzed Direct Reactions of Silicon, 1993 Elsevier Science Publishers B.V., pp. 1–66.

*Primary Examiner*—Paul F. Shaver
*Attorney, Agent, or Firm*—Noreen C. Johnson; Douglas E. Stoner

[57] ABSTRACT

A method is provided for improving alkylhalosilane selectivity in the direct method for making alkylhalosilane. There is introduced into the alkylhalosilane reactor, an effective amount of an organophosphine, such as trimethylphosphine, to enhance the formation of dialkylhalosilane during the direct reaction of alkylhalide and particulated silicon-copper contact mass.

11 Claims, No Drawings

6,005,130

METHOD FOR MAKING ALKYLHALOSILANES

BACKGROUND OF THE INVENTION

The present invention relates to a method for enhancing the proportion of dialkyldihalosilane in an alkylhalosilane mixture produced during the direct reaction of powdered silicon, alkylhalide and copper catalyst. More particularly, the present invention relates to the employment of a volatile promoter, for example, an organophosphine, such as a trialkylphosphine, to enhance the proportion of dialkyldihalosilane in an alkylhalosilane direct method mixture.

As shown by Rochow, in U.S. Pat. No. 2,380,995, a mixture of alkylhalosilanes can be obtained by the direct reaction between powdered silicon and an alkylhalide in the presence of a copper-silicon alloy, which is referred to hereinafter as the "direct method". Among the principal alkylhalosilanes formed by the direct method using methyl chloride, there are included methyltrichlorosilane, referred to hereinafter sometimes as "T", and dimethyldichlorosilane, referred to hereinafter sometimes as "D". D has the highest commercial interest, because it is the source material of choice, and methods for reducing the T/D ratio in direct method alkylhalosilane mixtures are of significant interest to the organosilicon industry.

Significant improvements in direct method alkylhalosilane product selectivity are provided in the method of Ward et al, U.S. Pat. No. 4,500,724, incorporated herein by reference, by utilizing a powdered silicon-copper-zinc-tin "contact mass" which has been found to favor the formation of dialkyldihalosilane over alkyltrihalosilane. As shown in the Ward patent, there can be used a fluid bed, stirred bed, or fixed bed reactor. The term "contact mass" as used hereinafter, means a particulated material comprising silicon and copper, which can include promoters, such as zinc and tin. The contact mass can form after contact with alkylhalide and reaction conditions have substantially stabilized at temperatures in the range of about 250° C. to 350° C. Alternatively, "pre contact mass" can be formed prior to contact or reaction with alkylhalide, and can be prepared by heating mixtures comprising particulated silicon and copper salts, such as copper halide and optionally in combination with other metallic promoters, at temperatures in the range of about 280° C. to 400° C.

Additional techniques have been used to improve the yields of dialkyldihalosilane during direct method practice. For example, a promoter such as phosphorous in the elemental or combined form can be used. The use of metal phosphides, such as copper phosphide, is shown by Halm et al in U.S. Pat. No. 4,762,940. Degan et al, U.S. Pat. No. 5,059,706, show that an effective amount of certain volatile phosphorous compounds, for example, phosphorous trichloride, can be used to enhance the proportion of dialkyldihalosilane in the resulting alkylhalosilane mixture. More recently, elemental phosphorous has been used in combination with zinc, as shown in Halm et al, U.S. Pat. No. 5,596,119, and in Margaria et al, U.S. Pat. No. 5,714,131, employing a crystalline phase of metallurgical silicon having dissolved phosphorous.

While the prior art shows that phosphorous, either in the elemental or combined form can be effective as a promoter in the direct method for enhancing the production of dialkyldihalosilane, additional techniques for introducing phosphorous as a promoter into the direct method are constantly being sought. As taught by Degan et al, U.S. Pat. No. 5,059,706, phosphorous trichloride, has an advantage over non-volatile phosphorous compounds, such as copper phosphide or elemental phosphorous dissolved in metallurgical silicon. For example, phosphorous trichloride does not require a metallurgical pretreatment or the intimate mixing of solids in order to provide a reduced amount of phosphorous into contact with a catalytically activated surface. Moreover, a volatile phosphorous compound is often easier to handle and can be more directly admixed with the gaseous stream of alkyl halide fed into the reactor.

Experience has shown, however, that while phosphorous trichloride has certain advantages over non-volatile phosphorous compounds as previously set forth, it is not widely used as a promoter in the production of dialkyldihalosilane by the direct method; phosphorous trichloride has been found to provide only a temporary improvement in the increase of %D when used as a phosphorous promoter in the direct method.

BRIEF SUMMARY OF THE INVENTION

The present invention is based on the discovery that organophosphines, and preferably trialkylphosphines, such as trimethylphosphine, have been found to combine the advantages of phosphorous trichloride volatility, while providing a substantially sustained %D increase when used as a phosphorous promoter in the direct method. As used hereinafter, the expression "sustained %D increase", means that a continuous increase in %D is maintained over a measured reaction period which can be expressed as % silicon utilization. The expression "improvement in crude selectivity" means that an increase in %D is obtained in the recovered alkyihalosilane.

There is provided by the present invention, a method for making alkylhalosilanes by the direct method, whereby an improvement in crude selectivity is achieved, comprising effecting reaction at a temperature in the range of about 280° C. to about 350° C. between (A) alkylhalide, and (B), a contact mass comprising powdered silicon, a copper catalyst, and an effective amount of zinc and tin, where there is used in the direct method reaction, an effective amount of an organophosphine.

DETAILED DESCRIPTION OF THE INVENTION

The method of the present invention can be practiced in a fluid bed, stirred bed, or fixed bed reactor; it is preferred to employ a fluid bed reactor in a continuous manner. Among the $C_{(1-4)}$ alkylchlorides which can used in the direct method, in accordance with the practice of the invention, there are included, methylchloride, ethylchloride, and propylchloride, with methyl chloride being preferred.

The silicon present in the fluidize bed can have a particle size up to 700 microns, and an average particle size of greater than 20 microns and less than 300 microns. The mean diameter of the silicon particles is preferably in the range of about 100 to 150 microns.

In forming the copper catalyst, and particularly the copper-zinc-tin catalyst, there can be used, various copper compounds, such as carboxylic salts of copper, for example, copper formate and copper acetate, copper oxides, hopper halides such as cuprous chloride, elemental copper in the form of flake or powder. There can be used from about 0.5% to about 5% by weight copper, based on the weight silicon, and the copper can be elemental or in the combined form, such as a partially oxidized salt of copper. With respect to zinc, there can be present, about 0.01 to about 0.5% zinc, per part by weight silicon, where zinc can be present as metal, or as a halide of zinc. Tin can be present at about 5 to about 100 parts per million (ppm), based on weight of silicon; tin can be present as metal dust, a tin halide, an oxide of tin, tetramethyl tin, or an alkyl tin halide.

Organophosphines which can used in the practice of the invention are phosphorous compounds having a molecular weight between about 76 to about 1000, and preferably about 76 to about 250, and are included within the following formula,

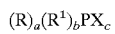

$(R)_a(R^1)_b PX_c$ where R is a $C_{(b\ 1-12)}$ alkyl radical, $R^1$ is a $C_{(6-9)}$ aryl radical, X is a halogen radical, "a" is a whole number equal to 0 to 3 inclusive, "b" is a whole number equal to 0 to 3 inclusive, "c" is a whole number equal to 0 to 2 inclusive, and the sum of "a","b", and "c" is equal to 3. Alkyl radicals included within R are for example, methyl, ethyl, propyl, and butyl; aryl radicals included within $R^1$ are for example, phenyl, tolyl, xylyl, halophenyl. Halogen radicals included within X, are for example, chloro, bromo, and fluoro.

Among the preferred organophosphines included within formula 1, are alkyl phosphines such as trimethyl phosphine, triethyl phosphine, tri-n-propyl phosphine, and tri-n-butyl phosphine and aryl phosphines such as triphenyl phosphine and tri-o-tolylphosphine. In addition, dimethylchlorophosphine and n-butyldichlorophosphine also can be used.

In the practice of the method of the invention, organophosphine is introduced into an alkyhalosilane reactor in an amount which is sufficient to serve as a promoter to effect a sustained improvement in the percent of dialkyldihalosilane formed in the resulting alkyhalosilane mixture. Effective dialkyldihalosilane selectivity results can be obtained if there is introduced into the reactor sufficient organophosphine to provide from about 100 ppm to about 1000 ppm of phosphorous, and preferably about 150 ppm to about 500 ppm of phosphorous based on weight of silicon.

While various alkyhalosilane reactors can be employed, it is preferred to introduce the organophosphine under continuous conditions in a fluid bed reactor. However, in instances where a fixed bed, or stirred bed reactor is used, appropriate adjustments can be made with respect to the manner and duration of organophosphine introduction. Depending upon such factors as the nature of the reactor, and the volatility of the organophosphine, the manner by which the organophosphine is introduced into the reactor can vary. For example, in some instances, the organophosphine can be added continuously, or periodically to the reactor with the alkyl halide in amounts sufficient to maintain the aforesaid parts per million level of phosphorous. In other situations, a solution of the organophosphine in an organic solvent also can be used.

In order that those skilled in the art will be able to practice the present invention, the following example is given by way of illustration, and not by way of limitation. All parts are by weight unless otherwise specified.

EXAMPLE

Methylchloride was continuously introduced at a temperature of 310° C. into a fluidized bed reactor having twenty grams of pre-contact mass of silicon powder, having 5% by weight copper and a starting Cu/Zn ratio of 100. Crude reaction product was collected and analyzed via gas chromatography over a 24 to 28 hour period.

The above procedure was repeated, except that 2 milligrams of chemically combined phosphorous, either as trimethylphosphine $P(CH_3)_3$ or phosphorous trichloride $(PCl)_3$ was respectively introduced with methylchloride into the reactor during the initial 60 to 90 minutes of methylchloride gas exposure.

Trimethylphosphine and phosphorous trichloride were respectively introduced into the reactor a total of three times as a 0.1M solution in toluene. Product crude was collected in each run over the course of 24 to 28 hours and analyzed via gas chromatography. Over the introduction period of the respective phosphorous compounds, an increase in D was determined for the three runs, based on a silicon utilization value of 35% by weight. The following results compare the respective average increase in D over the same silicon utilization value of 35% by weight in the reactor free of phosphorous promoter after the three runs, based on a standard deviation of 1.5:

|  | $PCl_3$ | $P(CH_3)_3$ |
|---|---|---|
| % D in crude | 88.3 | 92.8 |

The above results show that with a standard deviation of 1.5, there was a significant D increase obtained when trimethylphosphine of the present invention was used as a promoter, compared to phosphorous trichloride. It was also found that trimethylphosphine gave a sustained improvement in D increase, while phosphorous trichloride gave a reduced, less uniform increase in D.

What is claimed:

1. A method for making alkylhalosilanes by a direct method whereby an improvement in crude selectivity is achieved, comprising effecting reaction at a temperature in the range of about 250° C. to about 350° C. between (A) alkylhalide, and (B) a contact mass comprising powdered silicon and a copper catalyst, where there is used in the direct method reaction, an effective amount of an organophosphine.

2. A method in accordance with claim 1, where the contact mass comprises powdered silicon and a copper-zinc-tin catalyst.

3. A method in accordance with claim 1, where the alkylhalide is methylchloride.

4. A method in accordance with claim 1, where the organophosphine is trimethylphosphine.

5. A method in accordance with claim 1, where the reaction is conducted in a fluid-bed reactor.

6. A method in accordance with claim 1, where the organophosphine is triethylphosphine.

7. A method in accordance with claim 1, where the organophosphine is triphenylphosphine.

8. A method in accordance with claim 1, where the reaction is conducted in a fixed-bed reactor.

9. A method in accordance with claim 1, where the reaction is conducted in a stirred-bed reactor.

10. A method in accordance with claim 1, where a pre-contact mass is used in the direct method reaction.

11. A method in accordance with claim 1, where the organophosphine is introduced as an organic solvent solution.

* * * * *